US00PP35119P2

(12) United States Plant Patent
Rietberg

(10) Patent No.: US PP35,119 P2
(45) Date of Patent: Apr. 25, 2023

(54) ***HEBE* PLANT NAMED 'HL1802005'**

(50) Latin Name: ***Hebe* hybrid**
Varietal Denomination: HL1802005

(71) Applicant: Henrik Christiaan Cozijn Rietberg, Wezep (NL)

(72) Inventor: Henrik Christiaan Cozijn Rietberg, Wezep (NL)

(73) Assignee: EDEN'S CREATIONS B.V., Wezep (NL)

( * ) Notice: Subject to any disclaimer, the term of this patent is extended or adjusted under 35 U.S.C. 154(b) by 0 days.

(21) Appl. No.: 17/743,865

(22) Filed: May 13, 2022

(51) Int. Cl.
*A01H 5/02* (2018.01)
*A01H 6/68* (2018.01)

(52) U.S. Cl.
USPC ..... Plt./226
CPC ..... *A01H 6/68* (2018.05)

(58) Field of Classification Search
USPC ..... Plt./226
CPC ..... A01H 6/68; A01H 5/02
See application file for complete search history.

*Primary Examiner* — Keith O. Robinson
(74) *Attorney, Agent, or Firm* — Penny J Aguirre

(57) ABSTRACT

A new cultivar of *Hebe* plant named 'HL1802005' that is characterized by its consistently healthy plants that have a low susceptibility to leaf spot disease and downy mildew its compact plant habit, its small leaves, its flowers that are intense purple in color, and its floriferous blooming habit.

2 Drawing Sheets

Botanical classification: *Hebe* hybrid.
Cultivar designation: 'HL1802005'.

CROSS REFERENCE TO A RELATED APPLICATION

This application is related to a European plant breeders' rights application filed on Sep. 15, 2020, application No. 2020/2168. The Applicant received the information for the Plant breeders' rights application directly from the Inventor. This application is also co-pending with a U.S. Plant Patent Application filed for a plant derived from the same parentage that is entitled *Hebe* Plant Named 'HL1805002' (U.S. Plant patent application Ser. No. 17/743,909).

BACKGROUND OF THE INVENTION

The present invention relates to a new and distinct cultivar of *Hebe*, botanically of hybrid origin, known as *Hebe* 'HL1802005', and will be referred to hereafter by its cultivar name, 'HL1802005'. 'HL1802005' is an evergreen shrub grown for use as a container plant and as a landscape shrub.

The new cultivar was derived from a controlled breeding program conducted by the Inventor in Wezep, The Netherlands. The objectives of the breeding program is to select new cultivars of *Hebe* with improved plant health, compact plant habits, small leaves, abundant flowering, and self-cleaning flowers. The new cultivar arose from a cross made in August of 2017 between unpatented proprietary plants from the Inventor's breeding program; reference no. HM17-500 as the female parent and ref no. PM16-503 as the male parent. The Inventor selected 'HL1802005' in September of 2018 as a single unique plant amongst the seedlings that resulted from the above cross.

Asexual propagation of the new cultivar was first accomplished by stem cuttings in September of 2018 by the Inventor in Wezep, The Netherlands. Asexual propagation by stem cuttings and tissue culture using meristematic tissue has determined the characteristics of the new cultivar are stable and reproduced true to type in successive generations.

SUMMARY OF THE INVENTION

The following traits have been repeatedly observed and represent the characteristics of the new cultivar, which in combination distinguish 'HL1802005' as a new and distinct cultivar of *Hebe*.

1. 'HL1802005' exhibits consistently healthy plants that have a low susceptibility to leaf spot disease and downy mildew.
2. 'HL1802005' exhibits a compact plant habit.
3. 'HL1802005' exhibits small leaves.
4. 'HL1802005' exhibits flowers that are intense purple in color.
5. 'HL1802005' exhibits a floriferous blooming habit.

The female parent of 'HL1802005' differs from 'HL1802005' in having a less compact plant habit, leaves that are lighter green in color, flowers that less intense purple in color, and in being less floriferous. The male parent of 'HL1802005' differs from 'HL1802005' in having a higher susceptibility to leaf spot disease and downy mildew, a more vigorous growth habit, flowers that are less intense purple in color, and a shorter blooming period. 'HL1802005' can be most closely compared to the cultivars 'H130011' (un-patented), 'Mohawk' (un-patented), and 'HL805002'. 'H130011' is similar to 'HL1802005' in flower and foliage coloration. 'H130011' differs from 'HL1802005' in having a less robust plant structure. 'Mohawk' is similar to 'HL1802005' in plant structure and in having a floriferous blooming habit. 'Mohawk' differs from 'HL1802005' in having a higher susceptibility to leaf spot disease and downy mildew lighter green leaves, longer inflorescences, and flowers that are lighter purple in color. 'HL1805002' is similar to 'HL1802005' in having disease resistance, plant habit, leaf size, and in being floriferous. 'HL1805002' differs in having flowers that are white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by All-Blooms and Floraxchange.

BRIEF DESCRIPTION OF THE DRAWINGS

The accompanying color photographs illustrate the overall appearance and distinct characteristics of the new *Hebe*. The photographs were taken of a 7-month-old plant of 'HL1802005' as grown outdoors in a 12-cm container in Wezep, The Netherlands.

The photograph in FIG. 1 is a side view of 'HL1802005' in bloom.

Figure 1:
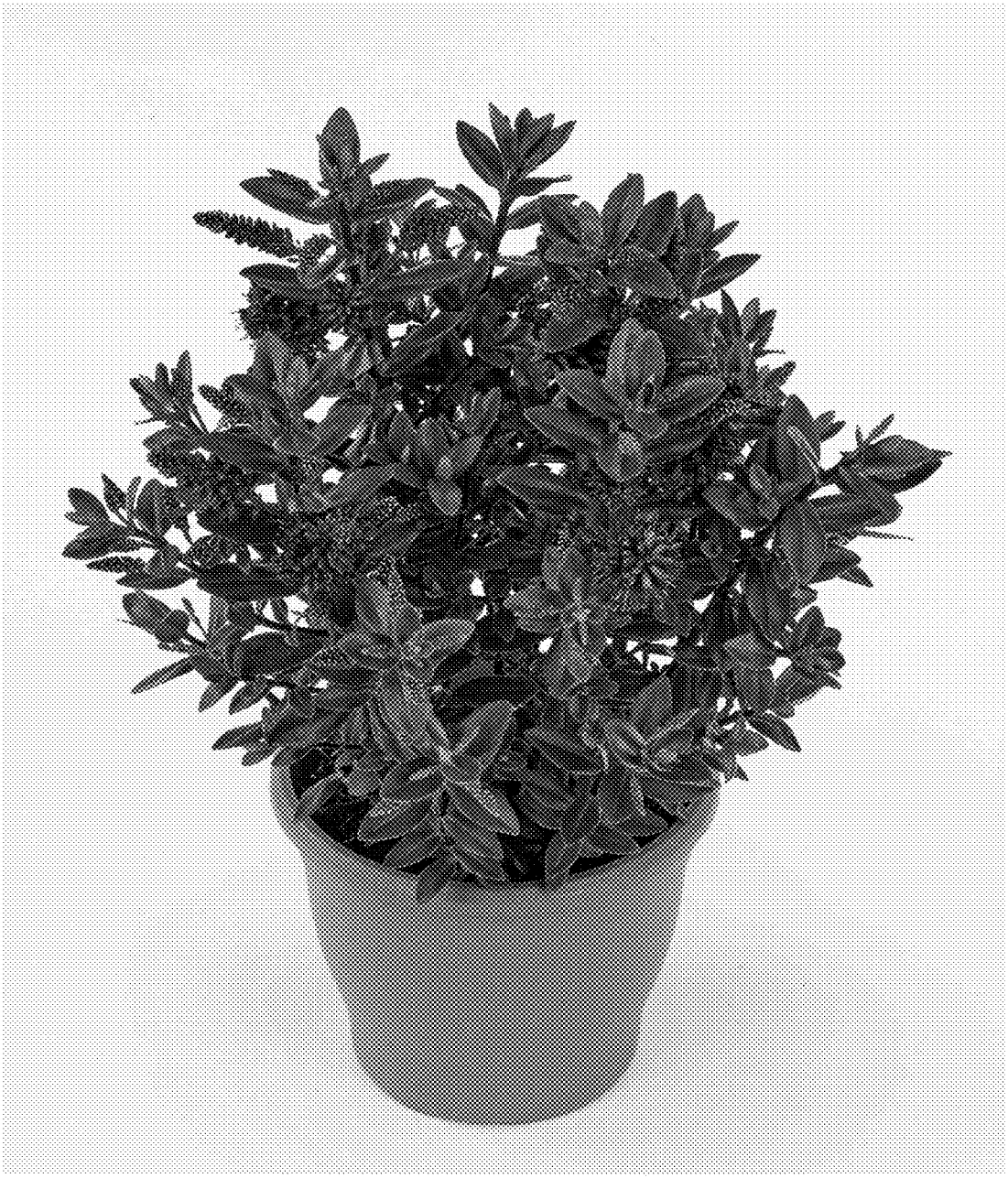
Figure 2:
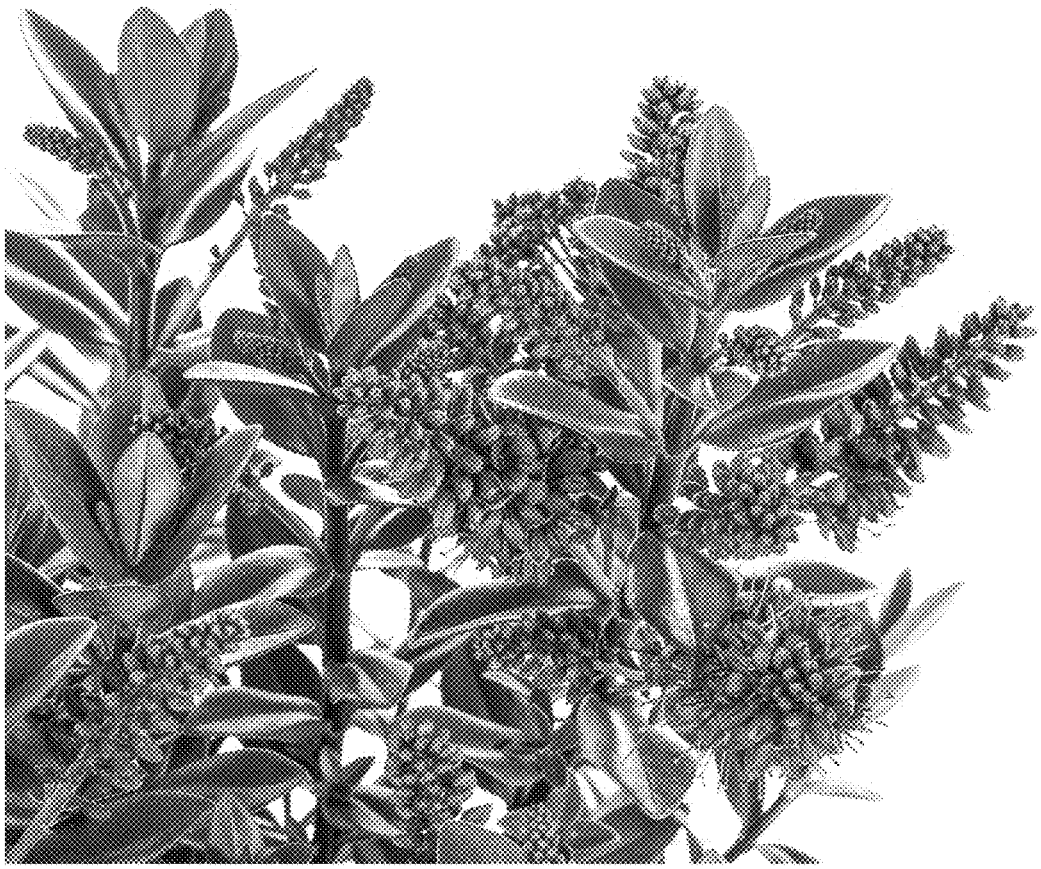

The photograph in FIG. 2 provides a close-up view of the inflorescences of 'HL1802005'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 12-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—An average of 5 weeks from summer into autumn in The Netherlands.

*Plant type*.—Evergreen shrub.

*Plant habit*.—Compact.

*Height and spread*.—Average of 22.6 cm in height and 22.4 cm in spread as a 7-month-old plant, an average of 70 cm in height and spread in the landscape.

*Hardiness*.—At least tolerant to U.S.D.A. Zone 8.

*Diseases and pest*.—Low susceptibility to leaf spot disease (*Septoria veronicae*) and downy mildew (*Perenospora* ssp.) no susceptibility or resistance to pests has been observed.

*Root description*.—Fibrous to slightly fleshy.

*Propagation*.—Softwood stem cuttings and tissue culture.

*Root development*.—3 to 4 weeks to initiate roots and 10 weeks to produce a young rooted plant.

*Growth rate*.—Moderate.

Branch description:

*Branch size*.—Lateral branches are an average of 13.4 cm in length and 2.5 mm in width.

*Branch shape*.—Round.

*Branch color*.—Young; N79A, mature; N186B and N186C.

*Branch surface*.—Densely covered with very short glandular hairs; 0.1 mm in length, matches surface color.

*Branch strength*.—Strong.

*Internode length*.—Average of 1.2 cm.

*Branching habit*.—Very freely branched from base, average of 27 primary branches.

Foliage description:

*Leaf shape*.—Narrow obovate, slightly carinate.

*Leaf division*.—Single.

*Leaf base*.—Cuneate.

*Sinus of the leaf bud*.—Present.

*Position of the broadest part of leave blade*.—In middle.

*Leaf apex*.—Bluntly acute.

*Leaf venation*.—Pinnate, upper surface; 147C to 147D, lower surface; 147A.

*Leaf margins*.—Entire, slightly coarsely undulate.

*Leaf attachment*.—Sessile.

*Leaf arrangement*.—Opposite.

*Leaf surface*.—Both surfaces smooth, glabrous, non-rugose, upper surface moderately glossy, lower surface matte to very slightly glossy.

*Leaf color*.—Young upper surface; a blend of 137C and 143A, young lower surface; N77A and N186C, mature upper surface; NN137B, mature lower surface; 146B.

*Leaf number*.—Average of 14 per lateral branch 13 cm in length.

*Leaf size*.—An average of 2.3 cm in length and 1 cm in width.

Flower description:

*Inflorescence type*.—Raceme.

*Shape in profile of the inflorescence*.—Triangular.

*Inflorescence size*.—Average of 4.9 cm in height and 2 cm in width.

*Inflorescence lastingness*.—About 7 days, self-cleaning.

*Flower shape*.—Campanulate.

*Flower fragrance*.—None.

*Flower quantity*.—Average 50 florets per inflorescence, 500 flowers per plant, 3,500 flowers and flower buds per plant.

*Inflorescence arrangement*.—Axillary racemes (lateral only).

*Flower aspect*.—Outward.

*Flower size*.—Average of 9 mm in height, 8 mm in diameter, 1 cm in depth, throat diameter 1.75 mm, flower tube length 3 mm, flower tube diameter 2.25 mm.

*Peduncles*.—Strong strength, 4.2 cm in length and about 1.5 mm in diameter, 144A in color, held at about a 40° angle to vertical, surface is very slightly glossy and densely covered with very short glandular hairs an average of 0.1 mm in length, matches surface color.

*Pedicels*.—Strong strength, average of 1.5 mm in length and 0.5 mm in diameter, held at about a 45° angle to peduncle, 146B in color.

*Flower buds*.—Narrow elliptic, 5.5 mm in length and 2 mm in diameter, color; 86A, immature calyx 146B, surface is matte, smooth and glabrous.

*Calyx*.—Rotate-shaped, average of 2 mm in length and 1.75 mm in diameter.

*Sepals*.—4, ovate in shape with entire margins, 2 mm in length, 1 mm in width, arrangement; rotate and campanulate, acute tip, base cuneate and fused, surfaces dull and smooth, color: when opening and fully open upper surface; 146B, lower half 146C, when opening and fully open lower surface; 146B, tinged 70C at the margins, lower half 146C.

*Petals*.—Average 4, 1 whorl, oblanceolate in shape, lower 42.5% of base is fused, about 4 mm in length and 2.5 mm in width, entire and slightly concave margins, apex obtuse, upper and lower surface is smooth and glabrous, non-rugose, upper surface matte to very slightly glossy, lower surface very slightly glossy, color: upper surface when opening; 86A, lower surface when opening; 83B, upper surface when fully open; 86B, lower surface when fully open; 83B, throat color; N82A, tube color; N82B.

*Floral bracts*.—A single bract is placed below each individual flower, very short oblong in shape, tip bluntly acute, cuneate base, 1 mm in length, 0.5 mm in width, both surfaces glabrous, color both surface; 146B in color, margins 70C.

Reproductive organs:

*Gynoecium*.—Pistil; 1, 7.5 mm in length, stigma; club-shaped, N79A in color, style; 7 mm in length and N81A in color, ovary; 144A in color.

*Androecium*.—Stamens: 2, anthers; dorsifixed, oblong in shape, 1.25 mm in length, 0.5 mm in width and 183B in color, filaments; 7 mm in length, color; N88B, fading slightly towards the distal end N88C, pollen; none observed.

*Fruit and seed*.—None observed to date.

It is claimed:

1. A new and distinct cultivar of *Hebe* plant named 'HL1802005' as herein illustrated and described.

* * * * *